United States Patent [19]

Meier et al.

[11] Patent Number: 5,512,679

[45] Date of Patent: Apr. 30, 1996

[54] PROCESS FOR THE PREPARATION OF 2-ARYL-ETHANE-SULPHONIC ACIDS

[75] Inventors: Jurgen-Dietrich Meier; Christian Munster; Volker Kass, all of Leverkusen, Germany; Horst Siffrin, New Martins Ville, W. Va.

[73] Assignee: Bayer Aktiengesellschaft, Leverkusen, Germany

[21] Appl. No.: 302,299

[22] Filed: Sep. 8, 1994

Related U.S. Application Data

[63] Continuation of Ser. No. 103,877, Aug. 6, 1993, abandoned.

[30] Foreign Application Priority Data

Aug. 14, 1992 [DE] Germany .......................... 42 27 027.8

[51] Int. Cl.$^6$ .................... C07D 213/34; C07D 211/24; C07D 265/30; C07D 487/08
[52] U.S. Cl. .......................... 546/339; 540/556; 544/170; 546/248; 548/186; 548/215; 548/342.1; 548/570; 562/30; 562/39; 562/40
[58] Field of Search ..................... 546/339, 248; 562/30, 39, 40; 540/556; 544/170; 548/186, 215, 342.1, 570

[56] References Cited

U.S. PATENT DOCUMENTS

| 2,508,904 | 5/1950 | Cislak | 546/339 |
| 3,479,397 | 11/1969 | Norton et al. | 562/30 |

FOREIGN PATENT DOCUMENTS 1643585 7/1971 Germany .................................. 562/30

OTHER PUBLICATIONS

Derwent abstract, Pharmaceuticals. p. 7, J6 0178.863–A Sep. 12, 1985.
Chemical Abstracts, vol. 84, Jun. 7, 1976, No. 23, Abst. No. 163,811(P).
Chemical Abstracts, vol. 104, Mar. 3, 1986, No. 9, Abst. No. 104:68760U.

*Primary Examiner*—Alan L. Rotman
*Attorney, Agent, or Firm*—William C. Gerstenzang; Sprung Horn Kramer & Woods

[57] ABSTRACT

2-aryl-ethane-sulphonic acids of the formula $$Ar^1-CH_2-CH_2-SO_3H \quad (I),$$

in which
 $Ar^1$ denotes a carbocyclic or heterocyclic aromatic radical which can be bound to an anellated benzene nucleus, can be obtained by reaction of the underlying vinyl aromatic compound with sulphurous acid, if the reaction is carried out in the presence of an amine of the formula $$N(R^1,R^2,R^3) \quad (III),$$

in which
 $R^1$, $R^2$ and $R^3$ have the meaning mentioned in the description.

10 Claims, No Drawings

PROCESS FOR THE PREPARATION OF 2-ARYL-ETHANE-SULPHONIC ACIDS

This application is a continuation, of application Ser. No. 08/103,877, filed Aug. 6, 1993, abandoned.

The invention relates to a process for the preparation of 2-aryl-ethane-sulphonic acids by reaction of the underlying vinyl aromatic compounds with sulphurous acid, which is characterised in that the reaction is performed in the presence of an amine.

The title compounds are valuable intermediates; for example, 2-heteroaryl-ethane-sulphonic acids such as 2-[4]-pyridyl-ethane-sulphonic acid, are valuable intermediates for the production of photochemicals and pharmaceuticals. Such 2-aryl-ethane-sulphonic acids are obtained in a known manner by reacting the underlying vinyl aromatic compounds with $SO_2$. According to US 2,508,904, some pyridyl-ethane-sulphonic acids are obtained by reaction of the underlying vinyl-pyridines with $SO_2$ in an aqueous alcoholic medium. Instead of $SO_2$, $NaHSO_3$ can also be used. Since, in this case, dark-coloured by-products are formed, the pyridyl-ethane-sulphonic acid prepared in this manner is rather unsuitable for photochemicals; in such cases a complex recrystallisation associated with losses is required.

According to JP 60/178 863 (1985), the co-use of an organic solvent can be dispensed with and water alone can be employed as a reaction medium. However, the yield at 65.8% is only moderate.

It has surprisingly been found that 2-aryl-ethane-sulphonic acids are obtained in a smooth reaction if the reaction known from the literature is carried out in the presence of an amine described in more detail below.

The present invention relates to a process for the preparation of 2-aryl-ethane-sulphonic acids or salts thereof, which, in the form of the free acids, correspond to the formula

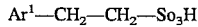

$$Ar^1\text{—}CH_2\text{—}CH_2\text{—}So_3H \qquad (I)$$

in which

Ar$^1$ denotes a carbocyclic or heterocyclic aromatic radical which can be bound to an anellated benzene nucleus, by reaction of vinyl aromatic compounds of the formula

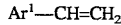

$$Ar^1\text{—}CH\text{=}CH_2 \qquad (II),$$

in which

Ar$^1$ has the above definition, with sulphurous acid or soluble salts thereof or the anhydride thereof in a water-containing medium, which is characterised in that the reaction is carried out at a temperature of −5° C. to +65° C. and at a pressure of 0.5 to 5 bar in the presence of an amine of the formula

$$N(R^1, R^2, R^3) \qquad (III)$$

in which

R$^1$, R$^2$ and R$^3$, independently of each other, denote straight-chain or branched $C_1$–$C_{12}$-alkyl, $C_3$–$C_8$-cycloalkyl, phenyl or substituted phenyl or $C_7$–$C_{10}$-aralkyl, where, furthermore, 2 of the radicals R$^1$, R$^2$ and R$^3$ together with the N atom which they substitute can form a 5- to 7-member saturated heterocyclic ring which can contain one or two further hetero atoms selected from the group comprising N, O and S, where, furthermore, up to two of the substituents R$^1$, R$^2$ and R$^3$ can denote hydrogen and where, furthermore, all three radicals R$^1$, R$^2$ and R$^3$ together with the N atom which they substitute can form a bicyclic tertiary amine or the pyridine system.

Ar$^1$ denotes a carbocyclic or heterocyclic aromatic radical which can be bound to anellated benzene nuclei. Carbocyclic radicals of this type are for example phenyl, naphthyl or biphenylyl, preferably phenyl. Such carbocyclic aromatic radicals can further be monosubstituted to trisubstituted by $C_1$–$C_4$-alkyl, such as methyl, ethyl, propyl, isopropyl, butyl, isobutyl, by $C_1$–$C_4$-alkoxy, such as methoxy, ethoxy, propoxy, isopropoxy, butoxy or isobutoxy, with chlorine, bromine or fluorine, preferably monosubstituted. Heterocyclic aromatic radicals are five-member rings or six-member rings having one or more hetero atoms selected from the group comprising N, S and O which can further be bound to an anellated benzene nucleus, such as the radicals of pyrrole, furan, thiophene, indole, thionaphthene, pyrazole, imidazole, benzimidazole, oxazole, thiazole, benzothiazole, triazole, pyridine, quinoline, isoquinoline, acridine, pyridazine, pyrimidine, pyrazine, thiazine, oxazine, quinoxaline, triazine and others familiar to those skilled in the art. Heterocyclic aromatic radicals of the type mentioned can themselves be substituted by $C_1$–$C_4$-alkyl, $C_1$–$C_4$-alkoxy, chlorine, bromine or fluorine.

The place of Ar$^1$ is preferably taken by the radical Ar$^2$, which denotes a heterocyclic aromatic radical which can be bound to an anellated benzene nucleus.

The place of Ar$^2$ is particularly preferably taken by the radical Ar$^3$ which denotes a pyridine radical, which can be bound to anellated benzene nuclei. Ar$^2$ and Ar$^3$ can also be substituted in the manner described under Ar$^1$.

In these cases, the vinyl aromatic compounds in question are those of the formulae

$$Ar^2\text{—}CH\text{=}CH_2 \qquad (IV)$$

or

$$Ar^3\text{—}CH\text{=}CH_2 \qquad (V)$$

Straight-chain or branched $C_1$–$C_{12}$-alkyl, in addition to the $C_1$–$C_4$-alkyl mentioned, denotes another of the isomeric pentyls, hexyls, octyls, decyls or dodecyls. $C_3$–$C_8$-cycloalkyl denotes cyclopropyl, cyclobutyl, cyclopentyl, cyclohexyl, cycloheptyl, cyclooctyl, methyl-or dimethyl-cyclopropyl, methyl- or dimethyl-cyclopentyl, methyl- or dimethyl-cyclohexyl or methyl-cycloheptyl.

Phenyl or substituted phenyl is a radical as has been described above under Ar$^1$.

$C_7$–$C_{10}$-aralkyl is, for example, benzyl, 1-phenyl-ethyl, 2-phenyl-ethyl, phenyl-propyl or phenyl-butyl, preferably benzyl, where the aromatic moiety can be substituted in the manner described above.

Two of the radicals R$^1$, R$^2$ and R$^3$ can, together with the N atom which they substitute, form a 5- to 7-member saturated heterocyclic ring. This can contain one or two further hetero atoms selected from the group comprising N, O and S. The compounds in question are then derivatives of cyclic amines of the pyrrolidine, oxazolidine, thiazolidine, piperidine or morpholine type and other compounds of this type known to those skilled in the art. Finally, all three radicals R$^1$, R$^2$ and R$^3$ together with the N atom which they substitute, can form a bicyclic tertiary amine such as DBU (diazabicycloundecane) or the pyridine system.

Suitable amines for the process according to the invention are, for example, triethylamine, tripropylamine, tributylamine, octyl-dimethylamine, N,N-dimethyl-cyclohexylamine, N-methyl-piperidine, N-methyl-morpholine, N,N-dimethyl-aniline, pyridine, or substituted pyridines.

Preferred amines for the process according to the invention are those of the formula

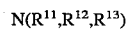  (VI), in which

R$^{11}$, R$^{12}$ and R$^{13}$, independently of each other denote straight-chain or branched C$_1$–C$_{12}$-alkyl, cyclopropyl, cyclopentyl, cyclohexyl or benzyl, where, furthermore, 2 of the radicals R$^{11}$, R$^{12}$ and R$^{13}$ together with the N atom which they substitute, can form a 5- to 7-member saturated heterocyclic ring which can contain one or two further hetero atoms selected from the group comprising N, O and S, where, furthermore, one of the substituents R$^{11}$, R$^{12}$ and R$^{13}$ denotes hydrogen or phenyl and where, furthermore, all three radicals R$^1$, R$^2$ and R$^3$ together with the N atom which they substitute, can form a bicyclic tertiary amine or pyridine system.

Particularly preferred amines for the process according to the invention are those of the formula

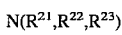  (VII)

in which

R$^{21}$, R$^{22}$ and R$^{23}$, independently of each other, denote straight-chain or branched C$_1$–C$_{12}$-alkyl, where, furthermore, one of the radicals R$^{21}$, R$^{22}$ and R$^{23}$ can denote cyclohexyl, phenyl or benzyl and where, furthermore, all three radicals R$^1$, R$^2$ and R$^3$, together with the N atom which they substitute, can form a bicyclic tertiary amine or the pyridine system.

The reaction of the vinyl aromatic compound is carried out with sulphurous acid H$_2$SO$_3$, or one of its water-soluble salts or its anhydride SO$_2$; the use of SO$_2$ is preferred in this case.

The molar ratios in question are: 1 to 5 mol, preferably 1.3 to 3.5 mol, particularly preferably 1.6 to 2.5 mol, of the amine described above per mole of vinyl aromatic compound. The molar ratio additionally in question is: 1 to 5 mol, preferably 1.3 to 3.5 mol, particularly preferably 1.6 to 2.5 mol, of sulphurous acid or its soluble salts or SO$_2$ per mole of vinyl aromatic compound. Amine and sulphurous acid or its soluble salts or SO$_2$ are further preferably used in an equimolar ratio to each other.

The process according to the invention, as exemplified by the reaction of 4-vinyl-pyridine with SO$_2$ in the presence of triethylamine in an aqueous medium, can be expressed in terms of formulae as given below:

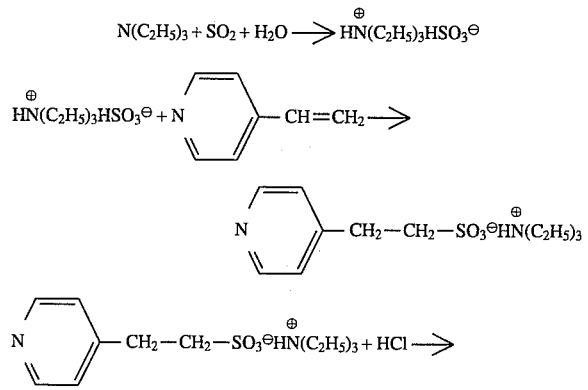

The process according to the invention is carried out at a temperature of −15° C. to +65° C., preferably at −10° to 65° C., particularly preferably at −5° C. to 40° C. It is not necessary to apply a superatmospheric or subatmospheric pressure. Therefore, the reaction is preferably carried out close to the atmospheric pressure, for example in a range from 0.5 to 5 bar, particularly preferably at atmospheric pressure.

The preferred performance of the process according to the invention close to room temperature and at atmospheric pressure produces only a low energy consumption and permits the use of simple apparatus.

The reaction medium for the process according to the invention is preferably water, since this is not accompanied by any further requirements for the recovery and recycling of organic solvents. However, it is equally possible to employ an aqueous/organic medium, if an amount of water at least equivalent to the sulphurous acid is present. Organic solvents which can be used in conjunction are C$_1$–C$_8$-alcohols, such as methanol, ethanol, propanol, isopropanol, butanol, isobutanol, amyl alcohol, hexanol or octanol; ketones such as acetone, methyl ethyl ketone, methyl isobutyl ketone; nitriles such as acetonitrile or cyclic ethers such as dioxane or tetrahydrofuran; it is alternatively possible also to use, in a mixture with water-soluble organic substances of the type mentioned, organic solvents which are miscible with water only with difficulty, such as dialkyl ether, toluene, cyclohexane or halogenated hydrocarbons. In addition to the preferred variant of water as a reaction medium, the co-use of such organic solvents of the type mentioned is also of importance, which solvents serve in the work-up of the exhausted reaction mixture to precipitate the resulting aryl-ethane-sulphonic acid.

To carry out the process according to the invention, for example, the amine and the water can be introduced and SO$_2$ can be passed into this introduced amount. The vinyl aromatic compound is added into such a prepared solution in which an ammonium hydrogen sulphite has formed. The weakly exothermic reaction is kept within the above-mentioned temperature range by suitable cooling or slight additional heating. If one of the above-mentioned organic solvents had not already been co-used as a reaction medium in addition to water, the precipitation of the 2-aryl-ethane-sulphonic acids or salts thereof is now induced by addition of such an organic solvent. For this precipitation, particularly the lower alcohols, such as methanol, ethanol or isopropanol have proved to be suitable. For the preferred case in which the 2-aryl-ethane-sulphonic acid shall be obtained in the form of its free acid, a strong acid, which leads to the formation of water-soluble salts, such as sulphuric acid, nitric acid, hydrochloric acid or hydrobromic acid, preferably hydrochloric acid, is added to the reaction batch containing the organic precipitant. Equally suitable are strong organic acids, such as sulphonic acids, halogenocarboxylic acids and others known to those skilled in the art. Because of the simple handling, hydrochloric acid is preferred, for example as HCl gas. The precipitation is advantageously promoted by cooling. The precipitated free acid is filtered off and washed using the precipitant.

The precipitant used can be recovered from the filtrates and washing waters by distillation and can be recycled. The distillation residue can then be worked up using alkali (alkaline earth) metal hydroxide to produce free amine, which is then recovered by distillation or phase separation and recycled; in the case of solid amines, filtration or extraction are also useful. Prior to distillation operations, residual SO$_2$ is preferably oxidised by an oxidising agent, for example hydrogen peroxide. In the case of higher amines, it can be sufficient to stir thoroughly an organic phase formed with water and then with dilute alkali (alkaline earth) metal hydroxide solution without oxidising the SO$_2$. In this manner, the amine is exclusively recovered by phase separation.

EXAMPLE 1390 ml =1012 g of triethylamine were placed in a 4 l four-necked glass flask and 815 ml of water were added. 640 g of sulphur dioxide were introduced at 15 to 25° C., and then stirred for the following 30 minutes. 532 g of 4-vinylpyridine (content approximately 98.0%) were added to this solution at 25° C. in accordance with the removal of heat. 2970 g =3760 ml of methanol were then added to the batch and 550 g of hydrogen chloride gas were then passed in. After cooling to 0°C., the precipitated 2-[4]-pyridyl-ethane-sulphonic acid was filtered and rinsed using 1500 ml of methanol in portions. Approximately 1440 g moist =920 g dry were obtained, content 96.5% =888 g of 100% (95.6% of the theoretical yield). The combined washings and mother liquors were treated with approximately 250 g of 30% strength hydrogen peroxide to destroy the sulphur dioxide, then the methanol was recovered by distillation. After addition of approximately 500 g of 50% strength sodium hydroxide solution, the amine was distilled off or recovered by phase separation.

What is claimed is:

1. A process for the preparation of 2-aryl-ethane-sulphonic acids and salts thereof, which, in the form of the free acids, correspond to the formula $$Ar^1\text{—}CH_2\text{—}CH_2\text{—}SO_3H \qquad (I),$$

in which

Ar$^1$ denotes phenyl or naphthyl which are unsubstituted or monosubstituted to trisubstituted by C$_1$–C$_4$-alkyl, C$_1$–C$_4$-alkoxy, chlorine, bromine or fluorine or a heterocyclic aromatic five-membered or six-membered radical having one or more N atoms as hetero atoms, and are unsubstituted or substituted by C$_1$–C$_4$-alkyl, C$_1$–C$_4$-alkoxy, chlorine, bromine or fluorine by reaction of vinyl aromatic compounds of the formula $$Ar^1\text{—}CH\text{=}CH_2 \qquad (II),$$

in which

Ar$^1$ has the above definition, with sulphurous acid or soluble salts thereof or the anhydride thereof in a water-containing medium, wherein the reaction is carried out at a temperature of −15° C. to +65° C. and at a pressure of 0.5 to 5 bar in the presence of an amine of the formula $$N(R^1, R^2, R^3) \qquad (III)$$

in which

R$^1$, R$^2$ and R$^3$, independently of each other, denote straight-chain or branched C$_1$–C$_{12}$-alkyl, C$_3$–C$_8$-cycloalkyl, phenyl or substituted phenyl or C$_7$–C$_{10}$-aralkyl, where, furthermore, 2 of the radicals R$^1$, R$^2$ and R$^3$ together with the N atom which they substitute can form a, pyrrolidine, oxazolidine, thiazolidine, piperidine or morpholine, where, furthermore, up to two of the substituents R$^1$, R$^2$ and R$^3$ can denote hydrogen and where, furthermore, all three radicals R$^1$, R$^2$ and R$^3$ together with the N atom to which they are attached form a diazabicycloundecane ring or a pyridine ring.

2. The process according to claim 1, wherein a vinyl aromatic compound of the formula $$Ar^3\text{—}CH\text{=}CH_2 \qquad (V)$$

is reacted, in which

Ar$^3$ denotes a pyridyl radical or an imidazolyl radical.

3. The process according to claim 1, wherein the reaction is carried out in the presence of an amine of the formula $$N(R^{11}, R^{12}, R^{13}) \qquad (VI)$$

in which

R$^{11}$, R$^{12}$ and R$^{13}$ independently of each other, denote straight-chain or branched C$_1$–C$_{12}$-alkyl, cyclopropyl, cyclopentyl, cyclohexyl or benzyl, where, furthermore, 2 of the radicals R$^{11}$, R$^{12}$ and R$^{13}$, together with the N atom which they substitute, can form a, pyrrolidine, oxazolidine, thiazolidine, piperidine or morpholine, where, furthermore, one of the substituents R$^{11}$, R$^{12}$ and R$^{13}$ denotes hydrogen or phenyl and where, furthermore, all three radicals R$^1$, R$^2$ and R$^3$, together with the N atom which to which they are attached form a diazabicycloundecane ring or pyridine ring.

4. The process according to claim 1, wherein the reaction is carried out in the presence of an amine of the formula $$N(R^{21}, R^{22}, R^{23}) \qquad (VII)$$

in which

R$_{21}$, R$^{22}$ and R$^{23}$, independently of each other, denote straight-chain or branched C$_1$–C$_{12}$-alkyl, where, furthermore, one of the radicals R$^{21}$, R$^{22}$ and R$^{23}$ can denote cyclohexyl, phenyl or benzyl and where, furthermore, all three radicals R$^1$, R$^2$ and R$^3$ together with the N atom to which they are attached form a diazabicycloundecane ring or pyridine ring.

5. The process according to claim 1, wherein a temperature from −10° to 65° C. is employed.

6. The process according to claim 1, wherein atmospheric pressure is employed.

7. The process according to claim 1, wherein 1 to 5 mol of amine are used per mole of vinyl aromatic compound.

8. The process according to claim 1, wherein 1 to 5 mol of sulphurous acid or its soluble salts or its anhydride are used per mole of vinyl aromatic compound.

9. The process according to claim 1, wherein in order to obtain the free sulphonic acids by precipitation after completion of the reaction, a strong mineral acid, which leads to the formation of water-soluble salts, is added, where the precipitation can be promoted by the presence of a water-miscible organic solvent.

10. The process according to claim 9, characterised in that after precipitation and filtration of the free sulphonic acids, alkali (alkaline earth) methal hydroxide is added to the filtrates and washing liquids and the amines thus liberated are recovered by distillation or phase separation and are recycled.

* * * * *

UNITED STATES PATENT AND TRADEMARK OFFICE
CERTIFICATE OF CORRECTION

PATENT NO. : 5,512,679
DATED      : April 30, 1996
INVENTOR(S): Meier, et al.

It is certified that error appears in the above-indentified patent and that said Letters Patent is hereby corrected as shown below:

Title page, item [57], ABSTRACT: Line 9 after " $R^3$ " insert -- ) --

Col. 6, line 37    Delete " $R_{21}$ " and substitute -- $R^{21}$ --

Signed and Sealed this

Twenty-ninth Day of October 1996

Attest:

BRUCE LEHMAN

Attesting Officer    Commissioner of Patents and Trademarks